(12) United States Patent
Pischlar

(10) Patent No.: US 11,590,314 B2
(45) Date of Patent: Feb. 28, 2023

(54) METHOD TO ADJUST CATHETER BODY MECHANICAL PROPERTIES VIA SELECTIVE COLD CRYSTALLIZATION IN CONTINUOUS PROCESSING

(71) Applicant: Medtronic, Inc., Minneapolis, MN (US)

(72) Inventor: Jesse Pischlar, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 770 days.

(21) Appl. No.: 16/578,463

(22) Filed: Sep. 23, 2019

(65) Prior Publication Data

US 2021/0085916 A1    Mar. 25, 2021

(51) Int. Cl.
*A61M 25/00* (2006.01)
*A61M 39/14* (2006.01)
*A61L 29/14* (2006.01)
*C08L 67/02* (2006.01)
*A61M 25/09* (2006.01)

(52) U.S. Cl.
CPC ......... *A61M 25/0012* (2013.01); *A61L 29/14* (2013.01); *A61M 39/146* (2013.01); *A61M 2025/09008* (2013.01); *A61M 2025/09108* (2013.01); *C08L 67/025* (2013.01)

(58) Field of Classification Search
CPC ............ A61M 25/0012; A61M 39/146; A61M 2025/09008; A61M 2025/09108; A61L 29/14; A61L 29/06; C08L 67/025; C08L 67/02; C08G 63/183; C08G 63/88
See application file for complete search history.

(56) References Cited

U.S. PATENT DOCUMENTS

| | | | |
|---|---|---|---|
| 8,182,466 B2 | 5/2012 | Stehr et al. | |
| 8,353,894 B2 | 1/2013 | Tegg et al. | |
| 8,585,753 B2 | 11/2013 | Scanlon et al. | |
| 8,684,999 B2 | 4/2014 | Tegg et al. | |
| 8,685,514 B2 | 4/2014 | Jeruzal et al. | |
| 8,974,426 B2 | 3/2015 | Corcoran et al. | |
| 9,114,229 B2 | 8/2015 | Fuentes | |
| 9,227,346 B2 | 1/2016 | McLeod et al. | |
| 9,855,371 B2 | 1/2018 | Scanlon et al. | |
| 9,950,141 B2 | 4/2018 | Fuentes | |
| 2009/0012500 A1* | 1/2009 | Murata | A61M 25/0012 604/525 |

(Continued)

*Primary Examiner* — Amber R Stiles
(74) *Attorney, Agent, or Firm* — Michael Best & Friedrich LLP

(57) ABSTRACT

A method of manufacturing tubing suitable for use as a component of a medical device, such as a catheter body, and the real-time adjustment of characteristics of the tubing as it passes from one reel to another reel during manufacture. Thus, a length of tubing is manufactured that includes a plurality of segments of different flexibilities and the length of tubing is then cut into a plurality of sub-lengths of tubing that are suitable for use as a component of a medical device. In one embodiment, a method of manufacturing a length of catheter tubing comprises: extruding a base layer; overlaying a braided layer on the base layer; overlaying a sub-jacket layer over the braided layer; overlaying an outer jacket on the jacket sub-layer; and heating at least a portion the jacket sub-layer to change a characteristic of the length of catheter tubing.

17 Claims, 9 Drawing Sheets

(56) References Cited

U.S. PATENT DOCUMENTS

| | | |
|---|---|---|
| 2012/0277671 A1 | 11/2012 | Fuentes |
| 2014/0243796 A1 | 8/2014 | Tegg et al. |
| 2015/0174365 A1 | 6/2015 | Corcoran et al. |
| 2015/0306282 A1 | 10/2015 | Scanlon et al. |
| 2015/0352326 A1 | 12/2015 | Tegg et al. |
| 2016/0303347 A1 | 10/2016 | Porter |
| 2017/0043129 A1 | 2/2017 | Fuentes |
| 2018/0169376 A1 | 6/2018 | Beeckler et al. |
| 2018/0282661 A1 | 10/2018 | Fuentes |
| 2018/0289925 A1 | 10/2018 | Palmer et al. |

\* cited by examiner

METHOD TO ADJUST CATHETER BODY MECHANICAL PROPERTIES VIA SELECTIVE COLD CRYSTALLIZATION IN CONTINUOUS PROCESSING

CROSS-REFERENCE TO RELATED APPLICATION n/a

FIELD

The present technology is generally related to methods of manufacturing tubing, such as tubing for use as a component of a medical device, and tubing formed as a result of such process.

BACKGROUND

Medical devices such as intravascular and intracardiac catheters are commonly used for a variety of medical procedures, such as in cardiovascular, neurologic, endoscopic, neurovascular, renal, and other applications. For example, these steerable devices may be used in minimally invasive procedures such as cardiac ablation, mapping, stent delivery, and imaging. In performing procedures such as these, it is often desirable, if not essential, that the catheter is sufficiently flexible, at least at the distal end, so the device can be steered through the patient's vasculature to the desired treatment location and properly positioned for treatment.

Manufacturing methods for tubing suitable for use as a component of a medical device, such as a catheter shaft or body, have improved over the years. Many types of tubing once required tedious hand assembly or time-intensive ram extrusion can now be produced using extrusion techniques that allow for multilayer extrusion of a device. However, although the manufacturing process is becoming more efficient, there are still several aspects of the production of catheter tubing and composite shafts that are inefficient and costly.

For example, many types of shafts are commonly produced using a discrete reflow and/or fusing method, in which a usable length of tubing for a catheter shaft, for example, less than six feet (such as around three feet), is processed at a time. As an example, a polymer tube is extruded and cut to a desired length, creating discrete polymer tubes. Each tube is then slid over a length of mandrel, and a reinforcement layer (for example, braided wire mesh or coiling) is overlaid onto each discrete tube. Then, another polymer tube is slid over the mandrel, first polymer tube, and reinforcement layer, and the whole assembly is heated in an oven to fuse the materials together under pressure of a compressive sleeve (such as a heat shrink layer) and create discrete lengths of catheter or sheath shaft. Undergoing each step for a discrete length of catheter or sheath is inefficient and adds increased labor requirements and operational costs while resulting in unit-to-unit-variability.

Additionally, it is often desired that the catheter shaft, and therefore the tubing, have varying flexural and/or torsional rigidities along its length. For example, a catheter body may have a distal portion that is less rigid than a proximal portion, or alternating segments of different rigidities, depending on the intended use of the medical device in which the catheter shaft is included. To create such a catheter shaft, individual segments are manufactured individually (or cut from a longer length of tubing having a uniform flexibility) and the segments are fused together or otherwise attached to each other to create the working length of tubing suitable for use as a catheter shaft. However, the joints at which the segments are attached to each other are prone to failure or breakage, even when complex joints or joints other than butt joints are used.

SUMMARY

The techniques of this disclosure generally relate to the manufacture of tubing suitable for use as a component of a medical device, such as a catheter shaft, and the real-time adjustment of characteristics of the tubing as it passes from one reel to another reel during manufacture. Thus, a length of tubing is manufactured that includes a plurality of segments of different flexibilities and the length of tubing is then cut into a plurality of sub-lengths of tubing that are suitable for use as a component of a medical device. In one embodiment, a method of manufacturing a length of catheter tubing comprises: extruding a base layer; overlaying a braided layer on the base layer; overlaying a sub-jacket layer over the braided layer; overlaying an outer jacket on the jacket sub-layer; and heating at least a portion of at least one from the group consisting of the base layer, the outer jacket layer, and the jacket sub-layer to change a characteristic of the length of catheter tubing.

In one aspect of the embodiment, the method is a reel-to-reel method.

In one aspect of the embodiment, the method further comprises cutting the length of catheter tubing to a plurality of sub-lengths of catheter tubing, each sub-length of catheter tubing being configured for use as an elongate body of a medical device. In one aspect of the embodiment, the medical device is a cardiac ablation catheter.

In one aspect of the embodiment, the base layer is at a first reel after the base layer is extruded.

In one aspect of the embodiment, overlaying the braided layer on the base layer includes passing the base layer from the first reel to a second reel, the base layer and the braided layer together being a first intermediate product; overlaying the jacket sub-layer on the braided layer includes passing the first intermediate product from the second reel to a third reel, the first intermediate product and the jacket sub-layer together defining a second intermediate product; overlaying the outer jacket on the jacket sub-layer including passing the second intermediate product from the third reel to a fourth reel, the second intermediate product and the jacket sub-layer together defining a third intermediate product; and heating the at least one portion of the jacket sub-layer includes passing the third intermediate product from the fourth reel to a fifth reel.

In one aspect of the embodiment, the third intermediate product is passed through a heating element.

In one aspect of the embodiment, the base layer includes a plurality of lumens.

In one aspect of the embodiment, the sub-jacket layer is at least partially composed of a crystallizable material.

In one aspect of the embodiment, the crystallizable material is polyethylene terephthalate (PET) and heating at least a portion the jacket sub-layer to change a characteristic of the length of catheter tubing includes at least partially crystallizing at least a portion of the PET.

In one aspect of the embodiment, heating at least a portion the jacket sub-layer includes heating the PET to a temperature above its glass transition temperature.

In one aspect of the embodiment, an entirety of the jacket sub-layer is heated.

In one aspect of the embodiment, less than an entirety of the jacket sub-layer is heated.

In one aspect of the embodiment, the jacket sub-layer is heated such that a plurality of segments having alternating flexibilities are created in a repeated pattern.

In one aspect of the embodiment, the jacket sub-layer is heated such that at least one segment having a first flexibility and at least one segment having a second flexibility are created, the first flexibility and the second flexibility being different.

In one embodiment, a method of manufacturing a length of catheter tubing comprises: extruding a base layer and passing the base layer to a first reel; overlaying a braided layer on the base layer as the base layer passes from the first reel to a second reel, the braided layer and base layer together being a first intermediate product; overlaying a sub-jacket layer over the braided layer of the first intermediate product as the first intermediate product passes from the second reel to a third reel, the sub-jacket layer and the first intermediate product together being a second intermediate product; overlaying an outer jacket on the jacket sub-layer of the second intermediate product as the second intermediate product passes from the third reel to a fourth reel, the outer jacket and the second intermediate product together being a third intermediate product; and heating at least a portion the jacket sub-layer of the third intermediate product as the third intermediate product passes from the fourth reel to a fifth reel to change a characteristic of the length of catheter tubing.

In one aspect of the embodiment, heating at least a portion of the jacket sub-layer includes passing the third intermediate product through a heating element between the fourth reel and the fifth reel.

In one aspect of the embodiment, the heating element is a reflow tower.

In one aspect of the embodiment, heating at least a portion of the jacket sub-layer includes adjusting a speed at which the third intermediate product passes from the fourth reel to the fifth reel and adjusting a time at which the at least a portion of the jacket sub-layer is exposed to the heating element.

In one embodiment, a method of manufacturing an elongate body of a medical device comprises: extruding a base layer, the base layer including a main lumen at a plurality of minor lumens, each of the main lumen and the plurality of minor lumens being without a liner; overlaying a braided layer on the base layer; overlaying a sub-jacket layer over the braided layer, the jacket sub-layer being at least partially composed of a crystallizable material; overlaying an outer jacket on the jacket sub-layer, the outer jacket being at least partially composed of a material that resists crystallization; heating the jacket sub-layer to change a flexibility of at least a portion of the length of catheter tubing; and cutting the length of catheter tubing into a plurality of sub-lengths of catheter tubing.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
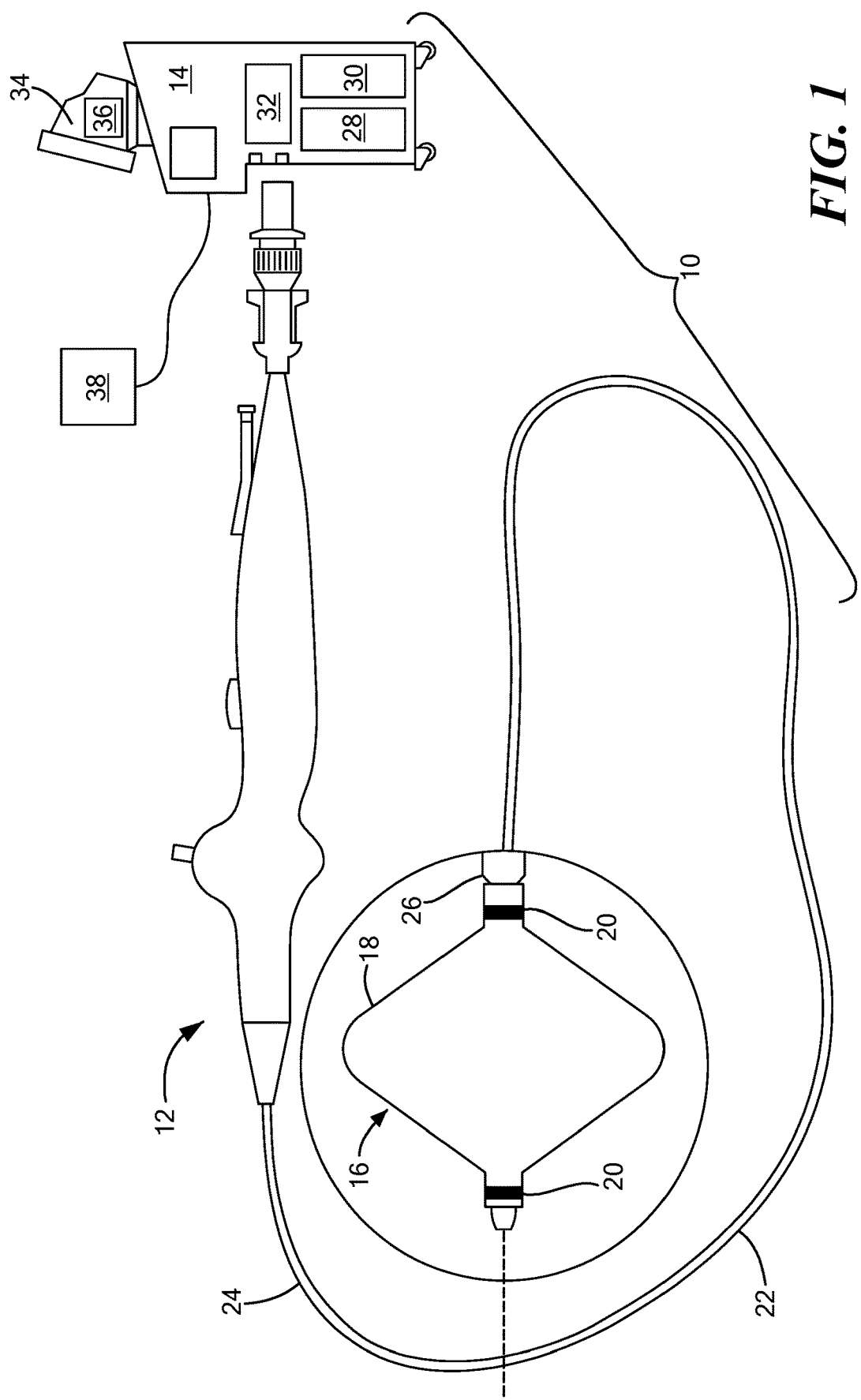
FIG. 1 shows an exemplary medical system that includes a medical device having a shaft and a treatment element at a distal portion of the shaft in accordance with the present disclosure.

The present invention advantageously provides methods of manufacturing tubing, such as tubing for use as a component of a medical device, and tubing manufactured as a result of such process. Referring now to the drawing figures in which like reference designations refer to like elements, an exemplary embodiment of a medical system including a medical device having a treatment element in accordance with principles of the present invention is shown in FIG. 1 and generally designated as "10." In one embodiment, the system 10 generally includes a medical device 12 that is coupled to a control unit or operating console 14. In one embodiment, the device 12 is a catheter that is configured to interact with tissue, such as with at least one treatment element 16. In one embodiment, the at least one treatment element 16 includes a balloon 18. Additionally or alternatively, the at least one treatment element 16 may include at least one electrode 20 with mapping and/or ablation functionality (not shown). It will be understood that the device 12 may include any elements for the treatment, analysis, or interaction with tissue and is not necessarily limited to those shown in the figures.

Continuing to refer to FIG. 1, the device 12 includes an elongate body 22 passable through a patient's vasculature and/or proximate to a tissue region for diagnosis and/or treatment. The elongate body 22 includes a proximal portion 24 and a distal portion 26, and may further include one or more lumens disposed within the elongate body 22 thereby providing mechanical, electrical, and/or fluid communication between the proximal portion of the elongate body 22 and the distal portion 26 of the elongate body 22. Exemplary lumens are shown in FIGS. 4, 6A, 6B, 8, and 10 and are discussed in more detail below. Further, in one embodiment the elongate body 22 of the device 12 is assembled using the catheter tubing formed by the method discussed herein.

Continuing to refer to FIG. 1, in one embodiment the system 10 is configured to perform a cryoablation procedure (for example, as shown in FIG. 1). In this embodiment, the system 10 may also include one or more fluid supply reservoirs 28, such as pressurized tanks, that include a coolant, cryogenic refrigerant, or the like in fluid communication with the treatment element 16. The system 10 may also include an exhaust or scavenging system for recovering or venting expended refrigerant for re-use or disposal and/or a fluid recovery reservoir 30. Further, although the fluid supply reservoir 28 and the fluid recovery reservoir 30 each may each located within or external to operating console 14, they are referred to as being part of the operating console 14 for simplicity. The operating console 14 may also include pumps, valves, controllers or the like to recover and/or re-circulate fluid delivered to the device 12. In another embodiment, the system is configured to perform another type of procedure, such as radiofrequency ablation, ultrasound ablation, laser ablation, mapping, diagnosis, or other procedures, alone or in combination with cryoablation. Thus, the operating console 14 may additionally or alternatively include energy generators 32, mapping systems, navigation systems, patch electrodes, or other suitable components.

Continuing to refer to FIG. 1, the operating console 14 may also include one or more controllers, processors, and/or software modules containing instructions or algorithms to provide for the automated operation and performance of the features, sequences, or procedures described herein. For example, the operating console 14 may include one or more computers 34 that include one or more processors 36 for receiving signals from one or more sensors throughout the system 10, and or for the automatic, semi-automatic, and/or manual operation of the system 10. The one or more computers 32 may include one or more user input devices 38 by which a user can program system parameters such as the inflation and deflation of a balloon 18, circulation of refrigerant through the fluid delivery and recovery conduits, and/or the operation of one or more electrodes 20 or other thermal delivery elements. The user input devices 36 may include keyboards, knobs, buttons, dials, foot pedals, mice, touchscreens, voice input units, and/or switches. Additionally, the user may use the user input devices to override the automatic operation of the system 10 either programmed into or predetermined by the operating console 14. Still further, signals received by the one or more processors 34 may be used to automatically or semi-automatically control the configuration of the at least one treatment element 16 or other part of the device 12. The one or more computers 32 may further includes one or more displays 38, such as computer screens or other visual elements in communication with the one or more processors 34 and/or user input devices 36. However, it will be understood that the system 10 may include additional or fewer components than those shown in FIG. 1, depending on the procedure for which the system 10 is configured.

Figure 2:
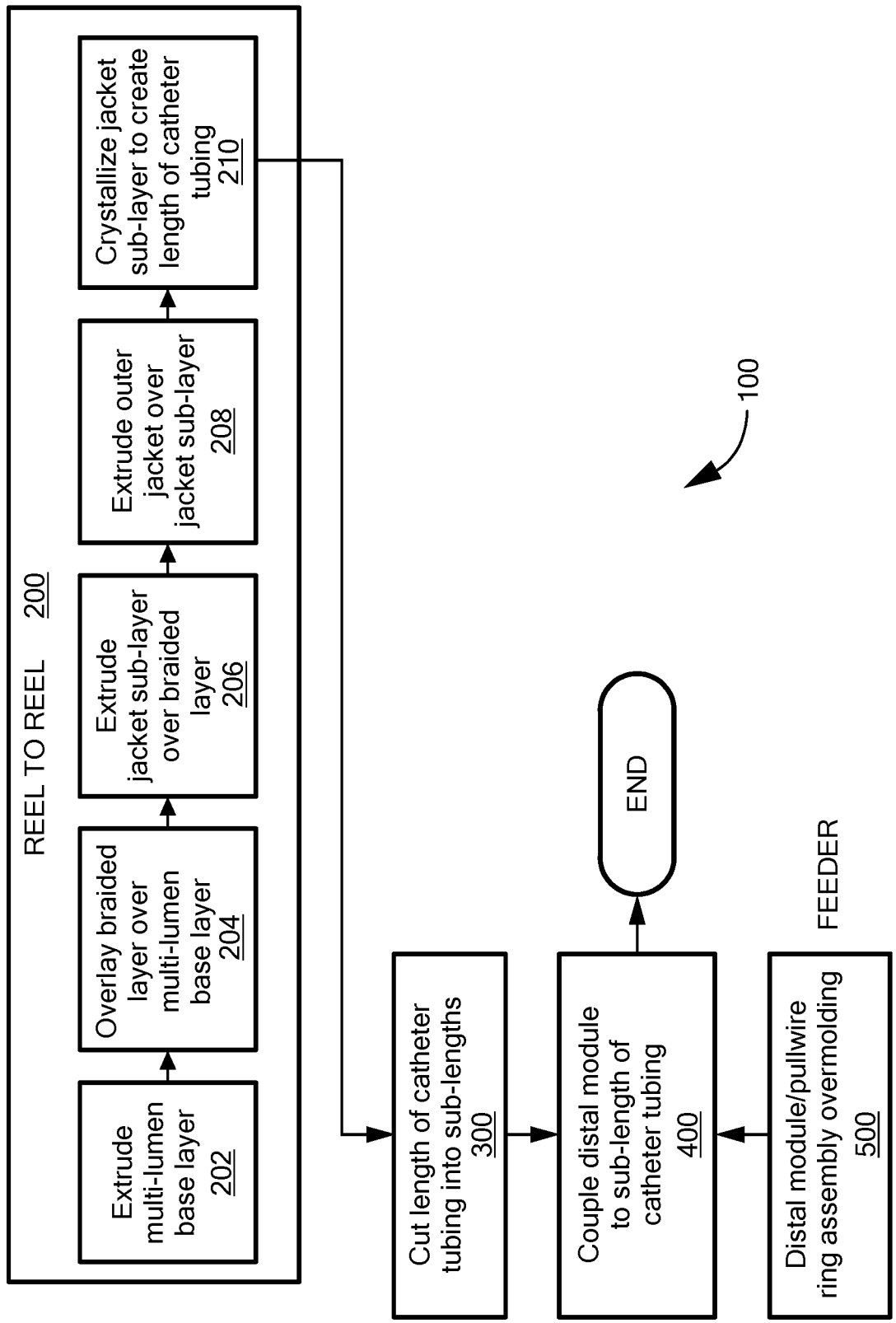
FIG. 2 is a flow chart showing an exemplary method of assembling a medical device in accordance with the present disclosure.

Referring now to FIG. 2, a flow chart of an exemplary method 100 of assembling a medical device 12 is shown. In one embodiment, the method 100 generally includes a first step 200 of reel-to-reel assembly (also referred to herein as continuous assembly or continuous processing) of a multi-layer catheter tubing 40 (or catheter body) and adjusting a mechanical property, such as flexibility, of at least a portion of the catheter tubing 40 during assembly. In one embodiment, the method 100 generally further includes a second step 300 of cutting the assembled catheter tubing 40 to length. In a non-limiting example of the reel-to-reel or continuous assembly process, layers are added to the catheter tubing 40 (that is, the catheter tubing 40 is created or assembled) as the catheter tubing 40 passes between reels 42 (or portions of the extrusion and assembly machinery 44). Regardless of the configuration of the extrusion and assembly machinery 44, the term "reel" is used herein for simplicity, and refers to a structure about or in which the catheter tubing (whether completed or in various stages of manufacture) may be wound or contained. That is, in some embodiments a reel 42 represents an "end" of the extrusion and assembly machinery 42 and is an endpoint to a particular step in the method of assembly. Further, although the method described includes the use of more than two reels 42, it will be understood that any number of reels 42 may be used and a particular reel may be reused. For example, the catheter tubing 40 may pass from a first reel 42A to a second reel 42B and then to a third reel 42C. Alternatively, the catheter tubing 40 may pass from the first reel 42A to the second reel 42B and then back to the first reel 42A.

Continuing to refer to FIG. 2, as the catheter tubing 40 passes between reels 42, one or more layers may be added and one or more additional steps, such as the selective application of heat treatment, braid density adjustment, on/off and/or selective polymer extrusion, may be performed. In one embodiment, the method further includes a third step 400 of coupling a distal module to one end of a length of cut catheter tubing. For example, the distal module may include the treatment element 16, a pullwire ring assembly, and/or other components, and the third step 400 may include coupling the distal module to a distal portion 26 of an elongate body 22 assembled using a cut length 40' of the catheter tubing 40. In some embodiments, the method further includes a fourth step 500 of overmolding at least a portion of the cut length 40' of the catheter tubing and/or the distal module to finalize assembly of the finished device 12. It will be understood that the third step 400 and the fourth step 500 may be performed in sequence, simultaneously, or in an alternate fashion as required to produce the desired finished device 12. However, it will be understood that once the length of catheter tubing 40 has been cut, one or more post-processing steps may be performed, such as attaching a hub, luer, or balloon, making holes, altering diameters, attaching marker bands and/or electrodes, plugging one or more lumens, etc.

Continuing to refer to FIG. 2, the first step 200 of method 200 of reel-to-reel or continuous assembly of catheter tubing 40 is now discussed in greater detail. In one embodiment, the catheter tubing 40 is used to assemble an elongate body 22 of the medical device 12. In one embodiment, the first step 200 includes a plurality of sub-steps that are performed to create a total length of catheter tubing 40 that is then cut to length (that is, cut into individual lengths 40' of catheter tubing, each of which being smaller in length than the total length of catheter tubing 40 and each being usable to assemble an elongate body 22 for a medical device 12). Further, in one embodiment, as the catheter tubing 40 passes from one reel to the next, the catheter tubing 40 is subject to one or more treatments, including the addition of multiple layers, braid density adjustments, on/off or alternating polymer extrusion, and/or other treatments or actions that affect the mechanical properties of the catheter tubing 40. In one embodiment, the total length of catheter tubing 40, and in some embodiments each individual length 40' of catheter tubing, has a plurality of segments with each segment having at least one characteristic that is different than characteristic(s) of at least one adjacent segments. For example, each segment may differ from at least one adjacent segment in one or more mechanical properties, such as durometer or flexibility, kink resistance, or the like. An exemplary elongate body 22 assembled using a length 40' of the catheter tubing 40 is shown and described in greater detail in FIGS. 12 and 13.

Continuing to refer to FIG. 2, in a first sub-step 202, a multi-lumen base layer 46 is extruded or created at a first portion of the extrusion and assembly machinery 44 by an extruder 48 and passed along a distance toward a first reel 42A. The multi-lumen base layer 46 is shown and described in greater detail in FIGS. 3 and 4. In a second sub-step 204, a braided layer 50 is added over the multi-lumen base layer 46 as the multi-lumen base layer 46 passes from the first reel 42A to a second reel 42B. The multi-lumen base layer 46 with braided layer 50 (which are collectively referred to herein as a first intermediate product 52) is shown and described in greater detail in FIGS. 5-6B. In a third sub-step 206, a jacket sub-layer 54 is extruded over the braided layer 50 as the first intermediate product 52 passes from the second reel 42B to a third reel 42C. The multi-lumen base layer 46, braided layer 50, and jacket sub-layer 54 (which are collectively referred to herein as a second intermediate product 56) are shown and described in greater detail in FIGS. 7 and 8. In a fourth sub-step 208, an outer jacket 58 is extruded over the jacket sub-layer 54 as the second intermediate product 56 passes from the third reel 42C to a fourth reel 42D. The multi-lumen base layer 46, braided layer 50, jacket sub-layer 54, and outer jacket 58 (which are collectively referred to herein as a third intermediate product 60) are shown and described in greater detail in FIGS. 9 and 10. The jacket sub-layer 54 and the outer jacket 58 may be collectively referred to herein as a jacket layer. In a fifth sub-step 210, shown and described in greater detail in FIGS. 11 and 12, at least a portion of the third intermediate product 60 is subjected to thermal treatment for a predetermined period of time sufficient to crystallize or otherwise affect the flexural rigidity at one or more areas along the third intermediate product 60 to a desired degree. Further, after thermal treatment, the third intermediate product 60 (or at least those portion(s) subjected to thermal treatment) is actively or passively cooled. Thus, the crystallization of the jacket sub-layer 54 may be referred to as cold crystallization. At completion of the fifth sub-step 210, the total length of the catheter tubing 40 having segments with varying flexibilities has been assembled. An exemplary device 12 that includes an elongate body 22 constructed using the catheter tubing 40 assembled according to the method of FIG. 2 is shown in FIG. 12. Thus, using this reel-to-reel method, a substantial length of complex catheter tubing 40 (for example, at least 100 feet or more) with segments of varying flexibilities and other mechanical properties may be quickly and easily assembled. This is in contrast to currently known methods of manufacturing such complex catheter tubing, in which an extruded tubing has to be cut into individual lengths and then custom assembled and completed according to individual requirements, which is time consuming and not cost-effective. Additionally, the catheter tubing 40 may be manufactured in a reel-to-reel process discussed herein to have any desired number of segments of varying flexibility and those segments may be of any desired length. Thus, if a device having an elongated body (catheter shaft) with segments having different flexibilities or other physical properties is desired, the need to glue, fuse, or otherwise attach multiple body segments together is eliminated, which may also reduce manufacturing and assembly costs and the likelihood of device failure or breakage at the joints.

Figure 3:
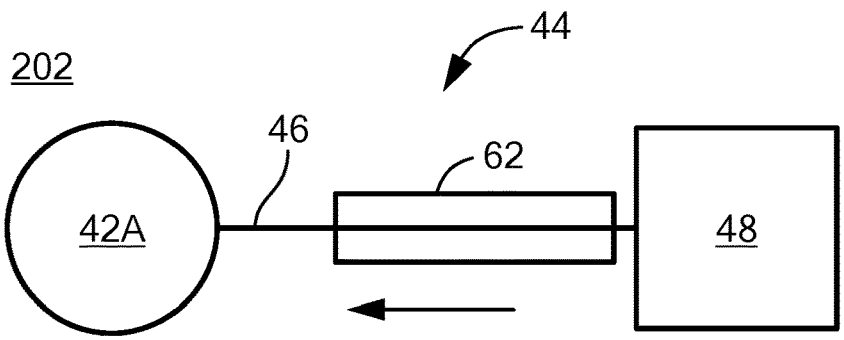
FIG. 3 is a stylized view of the first sub-step of a first step of the exemplary method of FIG. 2 in accordance with the present disclosure.

Referring now to FIG. 3, the first sub-step 202 of the method of FIG. 2 is shown in greater detail. As noted above, the multi-lumen base layer 46 is created by an extruder 48 in an extrusion process. In one embodiment, the multi-lumen base layer 46 is composed of a flexible material, for example, a polymer such as a thermoplastic copolyester (TPC-ET or TPC-ES, such as ARNITEL® thermoplastic copolymer), other thermoplastic elastomer, polybutylene terephthalate (PBT), polyether block amide (such as PEBAX® block copolymer), polyamide 12, high density polyethylene (HDPE), low density polyethylene (LDPE) or the like, and/or combinations thereof. As the multi-lumen base layer 46 is extruded, the temperature of the material is increased. Therefore, the multi-lumen base layer 46 it is immediately passed through an in-line water bath 62 as it is extruded to cool (quench) the multi-layer base layer 46 and prevent any undesired crystallization that may occur as a result of the increased temperature. As is discussed in greater detail below, the crystallinity and, therefore, the flexibility of the catheter tubing 40 is controlled in a later sub-step of the method and crystallization of catheter tubing 40 materials is avoided in the first sub-step 202. In one embodiment, a liner is not included in any lumen 64, 66 of the multi-lumen base layer 46. At the conclusion of the first sub-step 202, in one embodiment the multi-lumen base layer 46 is entirely or at least substantially wound about or contained within the first reel 42A.

Figure 4:
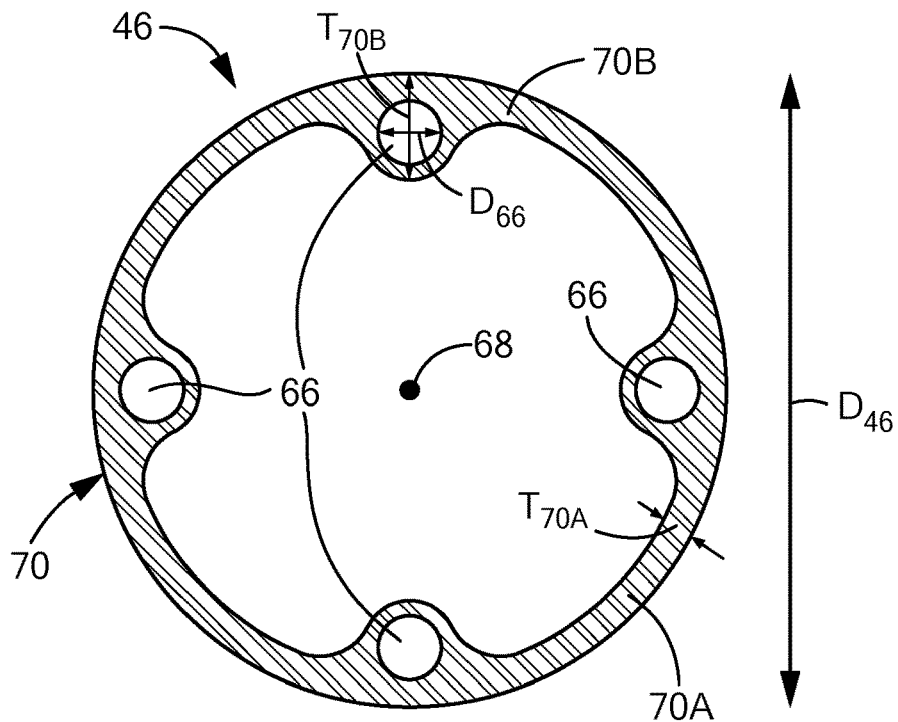
FIG. 4 is a cross-sectional view of a multi-lumen base layer created during the first sub-step of the exemplary method of FIG. 2 in accordance with the present disclosure.

Referring now to FIG. 4, a cross-sectional view of the multi-lumen base layer 46 created in the first sub-step 202 is shown. In one embodiment, the multi-lumen base layer 46 includes a main lumen 64 and two minor lumens 66. For example, one minor lumen 66 may be a pullwire lumen and the other minor lumen 66 may be a vacuum lumen. In one embodiment, each of the minor lumens 66 is approximately 0.008 inch (±0.002 inch) from the longitudinal axis of the multi-lumen base layer 46 (that is, from an imaginary center axis 68 of the multi-lumen base layer 46) and has a diameter $D_{66}$ of approximately 0.0125 inch (±0.005 inch). Further, in one embodiment the multi-lumen base layer 46 includes a wall 70 that defines an outer surface of the multi-lumen base layer 46. In one embodiment, the wall 70 has a first portion 70A that at least partially defines the main lumen 64 and has a first thickness $T_{70A}$, and a second portion 70B that defines the minor lumens 66 and has a second thickness $T_{70B}$. In the embodiment shown in FIG. 4, the first thickness $T_{70A}$ is less than the second thickness $T_{70B}$, and the second thickness $T_{70B}$ is greater than the diameter $D_{66}$ of each of the minor lumens 66. In one non-limiting example the first thickness $T_7OA$ is approximately 0.006 inch (±0.002 inch) and the outer diameter $D_{46}$ of the multi-lumen base layer is approximately 0.124 inch (±0.03 inch). Further, in one embodiment, no tube (such as a polyimide tube) is included in at least one of the minor lumens 66. The main lumen 64 of the multi-lumen base layer 46 may provide up to 40% more cross-sectional area than main lumens of currently known devices. In one embodiment, this is achieved by increasing the outer diameter of the shaft from a diameter of 0.138 inch, as is commonly used in existing devices, to 0.144 inch and maintaining the wall thickness (at approximately 0.016 inch). Additionally or alternatively, in some embodiments, the cross-sectional area is increased by reducing the wall thickness of the shaft (which may be facilitated by the crystallization of one or more layers of the shaft), thus opening more space in the main lumen. However, the ultimate design of the shaft may depend on the use of the device for which the shaft is intended.

Figure 5:
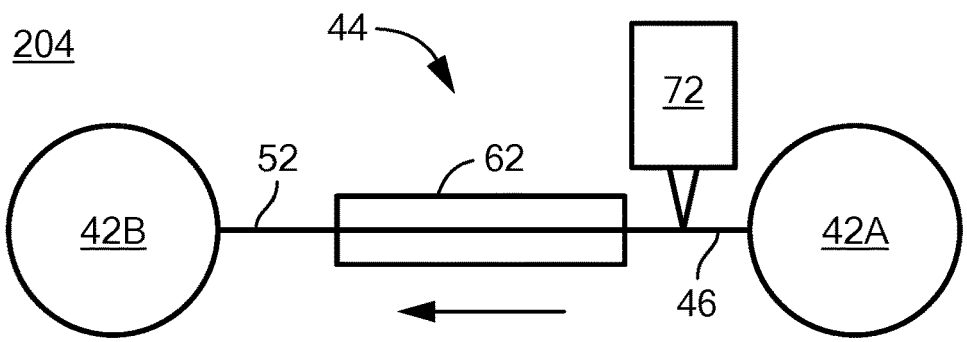
FIG. 5 is a stylized view of the second sub-step of the first step of the exemplary method of FIG. 2 in accordance with the present disclosure.

Referring now to FIG. 5, the second sub-step 204 of the method of FIG. 2 is shown in greater detail. As noted above, a reinforcement layer, such as a braided layer 50 or a coiled layer, is added over the multi-lumen base layer 46 in the second sub-step 204 to create the first intermediate product 52 as the multi-lumen base layer 46 passes from the first reel 42A to a second reel 42B. In one embodiment, the braided layer 50 is deposited by a braiding machine 72. Further, the density (braid angle) of the braided layer 50 may be changed in real time as the braided layer 50 is added, such as by adjusting the selected parameters in the braiding machine and/or the speed of the multi-lumen base layer 46 as it moves from the first reel 42A to the second reel 42B. If a coiled layer is used instead of a braided layer, one or more characteristics of the coiled layer, such as coil pitch, may be changed in real time. In one embodiment, the first intermediate product 52 is passed through an in-line water bath 62 after the braided layer 50 is added 50 to counteract any temperature increase caused by the addition of the braided layer 50. As is discussed in greater detail below, the crystallinity and, therefore, the flexibility of the catheter tubing 40 is controlled in a later sub-step of the method and crystallization of catheter tubing 40 materials is avoided in the second sub-step 204.

Figure 6A:
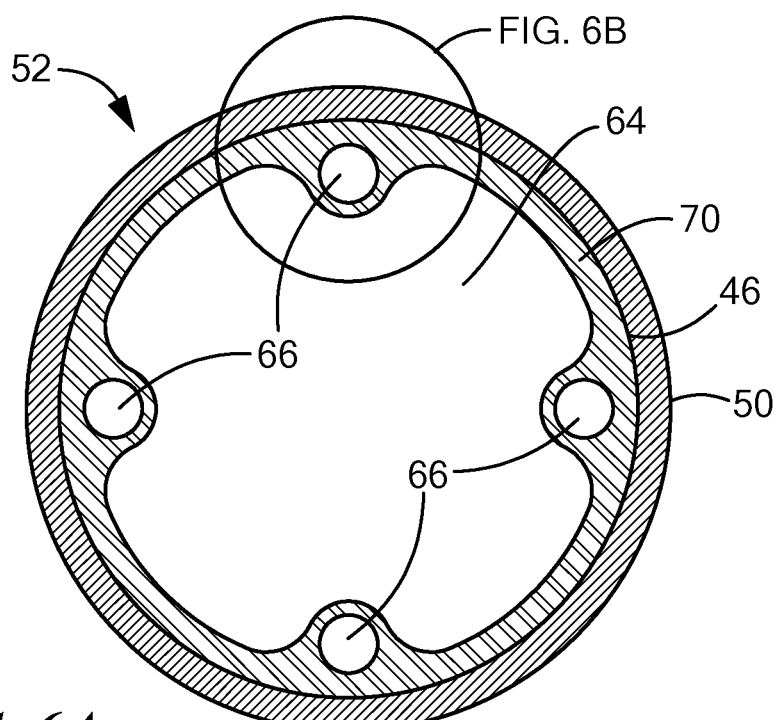
FIG. 6A is a cross-sectional view of a first intermediate product during the second sub-step of the exemplary method of FIG. 2 in accordance with the present disclosure.
Figure 6B:
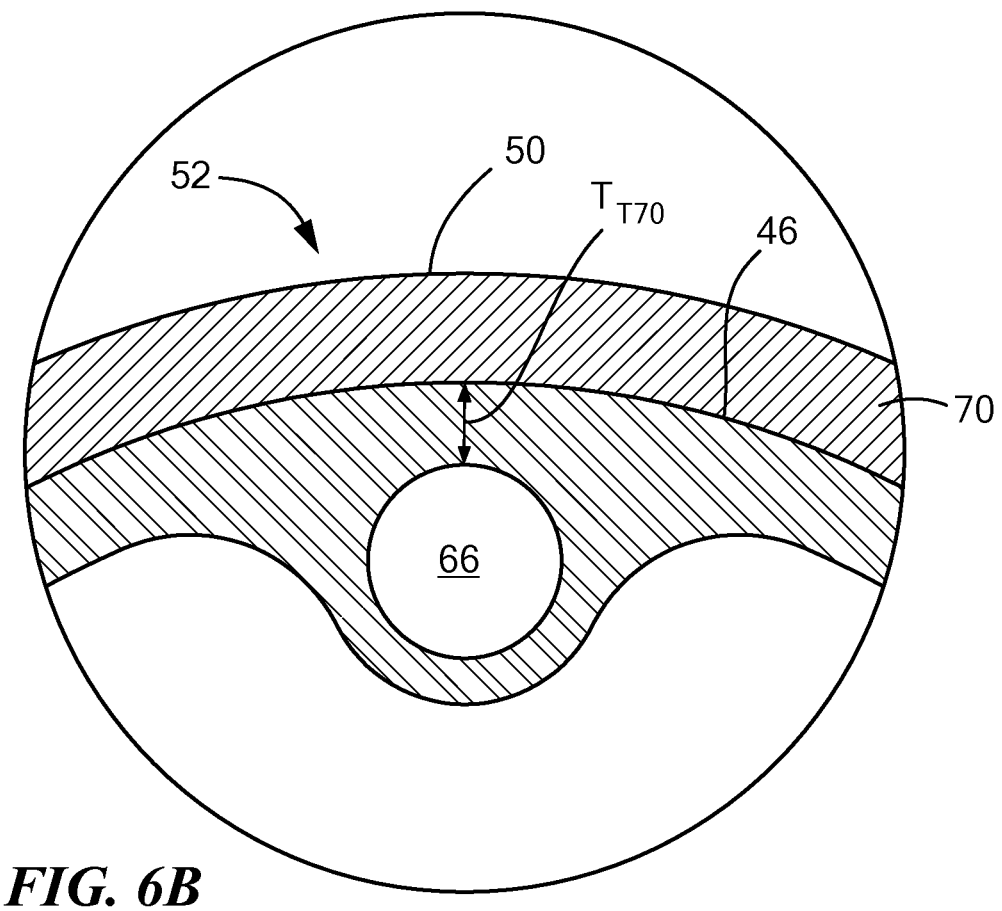
FIG. 6B is a close-up view of a portion of the cross-sectional view of FIG. 6A in accordance with the present disclosure.

Referring now to FIGS. 6A and 6B, a cross-sectional view of the first intermediate product 52 created in the second sub-step 204 is shown. In one embodiment, the braided layer 50 extends around the circumference of the multi-lumen base layer 46. Further, in one non-limiting example, the braided layer 50 is composed of a round metallic wire, such as 304V stainless steel wire with 0.002 inch diameter and a minimum tensile strength of 300 ksi min. Further, sixteen wires may be used, at approximately 65 pics per inch (PPI) (±5 PPI). However, it will be understood that the braided layer 50 may have a different composition, such as the number of wires used, the material from which the wires are composed, the diameter of the wires, the cold and heat treatments applied etc. In one embodiment, the thickness $T_{T70}$ of the wall 70 of the multi-lumen base layer 46 at its thinnest point between each minor lumen 66 and the braided layer 50 may be approximately 0.003 inch (±0.0005 inch).

Figure 7:
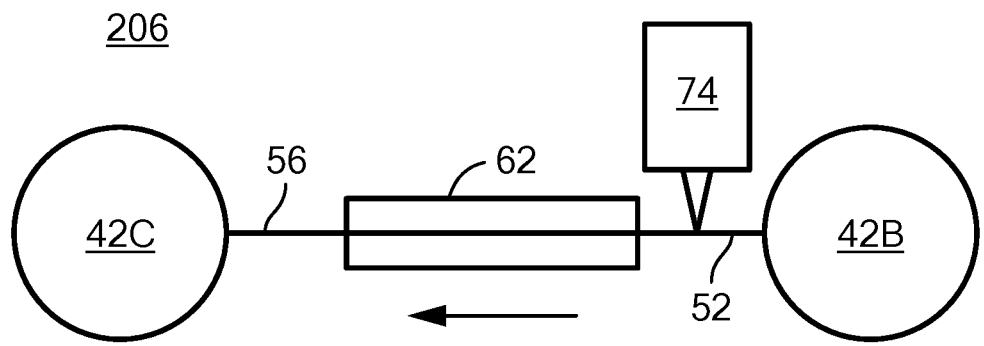
FIG. 7 is a stylized view of the third sub-step of the first step of the exemplary method of FIG. 2 in accordance with the present disclosure.

Referring now to FIG. 7, the third sub-step 206 of the method of FIG. 2 is shown in greater detail. As noted above, a jacket sub-layer 54 is extruded over the braided layer 50 to create the second intermediate product 56 as the first intermediate product 52 passes from the second reel 42B to a third reel 42C. In one embodiment, the jacket sub-layer 54 is added by an extruder 74. The jacket sub-layer 54 is at least partially composed of a crystallizable material. In one embodiment, the jacket sub-layer 54 is at least partially composed of polyethylene terephthalate (PET), such as PET in an amorphous or semi-crystalline state. PET is a thermoplastic polymer that may exist in an amorphous state, a crystalline state, or somewhere between. When in the crystalline state, the polymer chains are parallel and closely packed to each other. When in amorphous state, the polymer chains are disordered and, therefore, the material is more flexible or less rigid than when in the crystalline state. Crystallinity in PET (and other thermoplastic polymers) may be induced by heating the material above its glass transition temperature ($T_g$) and not reducing its temperature rapidly enough to allow it to return to the amorphous state. In one embodiment, the PET used for the jacket sub-layer 54 is at least partially composed of a material selected to resist crystallization or at least to have reduced crystallization rates to provide greater control over the crystallization of the jacket sub-layer 54 in later steps of the method 100 and to avoid undesired crystallization during extrusion of the PET and/or as the outer jacket 58 is extruded over the jacket sub-layer 54. For example, the PET from which the outer jacket 58 is composed may be Array® 9921M (DAK Americas LLC, Delaware). Immediately after the jacket sub-layer 54 is extruded over the braided layer 50 to create the second intermediate product 56, the second intermediate product 56 is passed through an in-line water bath 62 or other cooling element to quench the PET of the jacket sub-layer 54 to maintain the PET in the amorphous state (or prevent crystallization). As in the other sub-steps 202, 204, the crystallinity and, therefore, the flexibility of the catheter tubing 40 is controlled in a later sub-step of the method and crystallization of catheter tubing 40 materials is avoided in the third sub-step 206.

Figure 8:
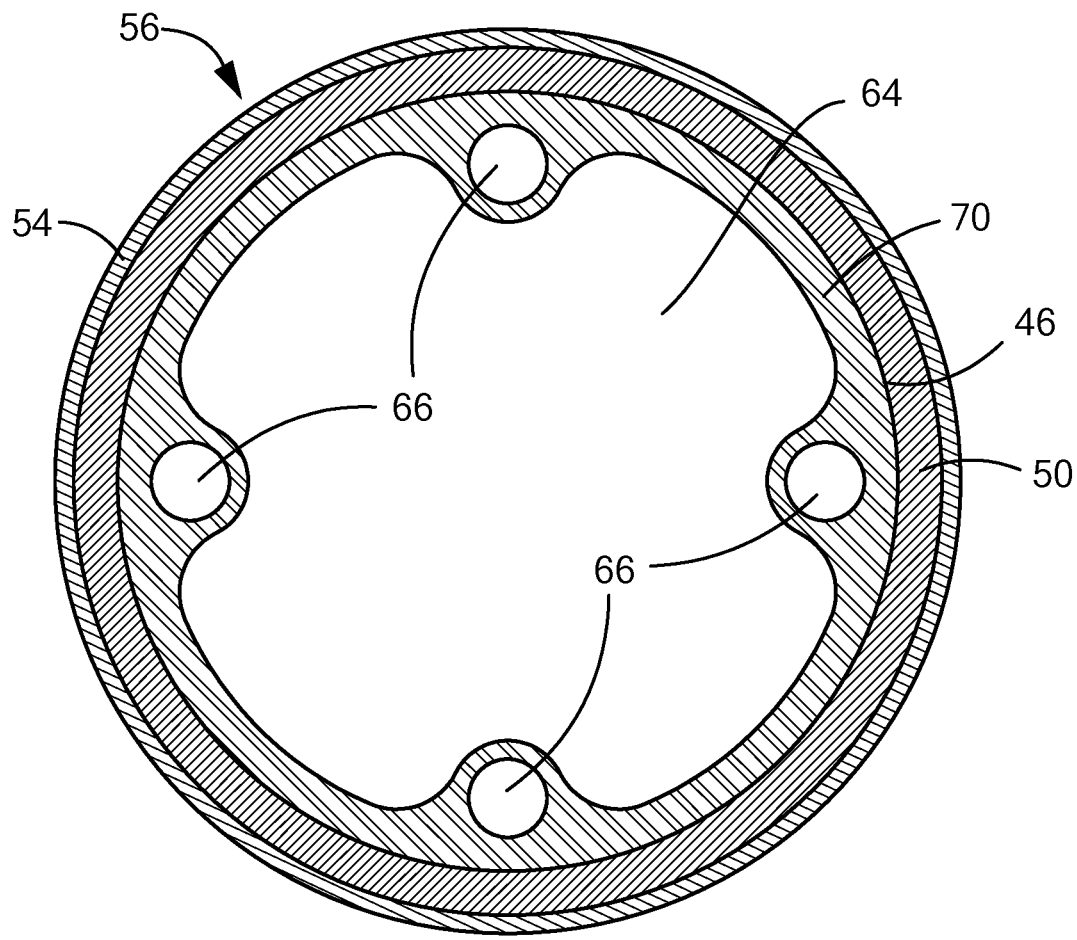
FIG. 8 is a cross-sectional view of a second intermediate product during the third sub-step of the exemplary method of FIG. 2 in accordance with the present disclosure.

Referring now to FIG. 8, a cross-sectional view of the second intermediate product 56 created in the third sub-step 206 is shown. In one embodiment, the jacket sub-layer 54 extends around the circumference of the first intermediate product 52. Depending on the density of the weave of the braided layer 50, the braided layer 50 may have one or open portions of the weave that expose the underlying multi-lumen base layer 46. Thus, although FIG. 8 shows the jacket sub-layer 54 as being separated from the multi-lumen base layer 46 by the braided layer 50, it will be understood that in some areas the jacket sub-layer 54 may flow through the openings of the braided layer 50 and come into contact with the multi-lumen base layer 46 as the jacket sub-layer 54 is extruded over the braided layer 50.

Figure 9:
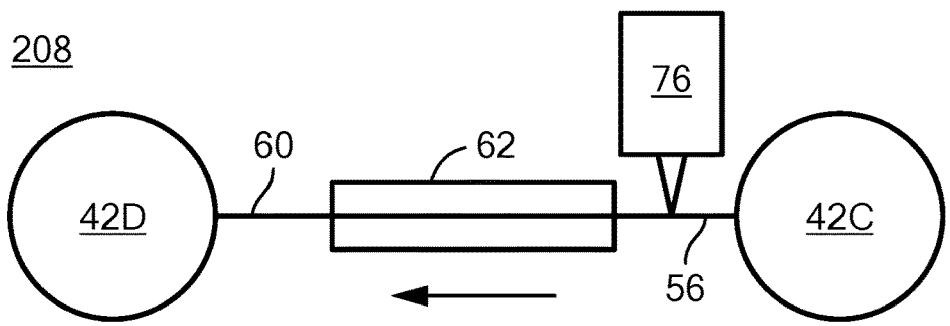
FIG. 9 is a stylized view of the fourth sub-step of the first step of the exemplary method of FIG. 2 in accordance with the present disclosure.

Referring now to FIG. 9, the fourth sub-step 208 of the method of FIG. 2 is shown in greater detail. As noted above, an outer jacket 58 is extruded over the jacket sub-layer 54 to create the third intermediate product 60 as the second intermediate product 56 passes from the third reel 42C to a fourth reel 42D. In one embodiment, the outer jacket 58 is added by an extruder 76. As noted above, the jacket sub-layer 54 may be composed of a PET that is engineered to have reduced crystallization rates (that is, a wide processing window). Additionally, in one embodiment the third intermediate product 60 is passed through an in-line water bath 62 immediately after the outer jacket 58 is extruded over the jacket sub-layer 54 to counteract any temperature increase caused by the extrusion of the outer jacket 58. As in the other sub-steps 202, 204, 206, the crystallinity and, therefore, the flexibility of the catheter tubing 40 is controlled in a later sub-step of the method and crystallization of catheter tubing 40 materials is avoided in the fourth sub-step 208.

Figure 10:
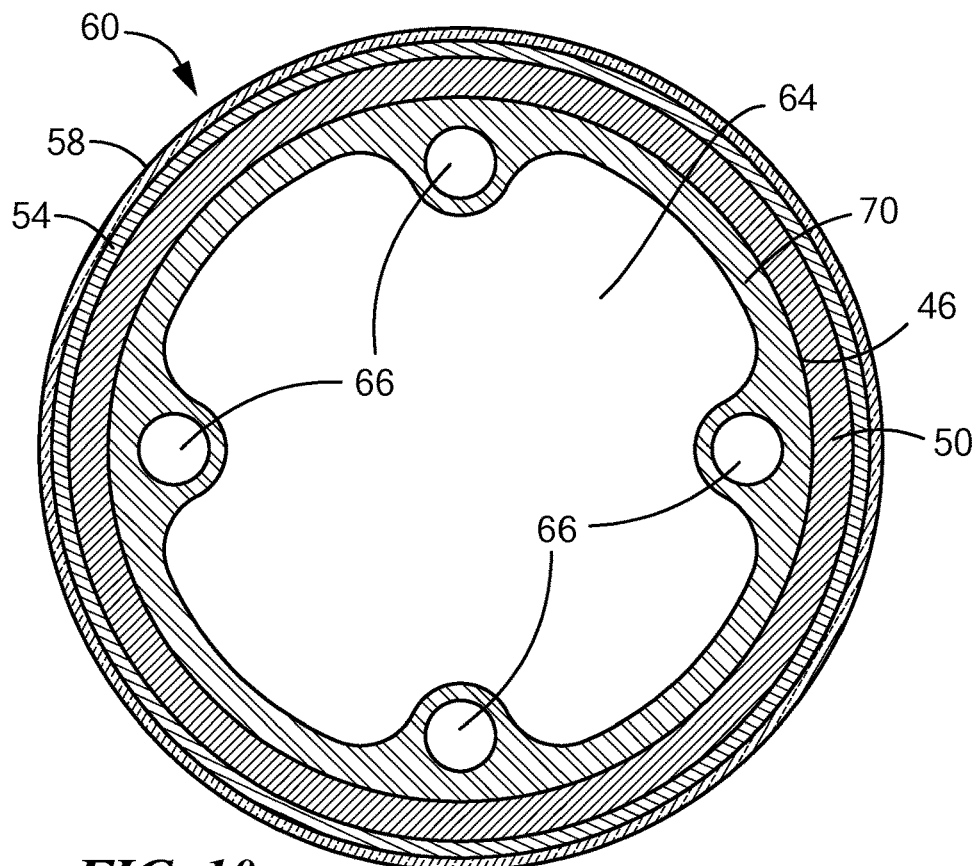
FIG. 10 is a cross sectional view of a third intermediate product during the fourth sub-step of the exemplary method of FIG. 2 in accordance with the present disclosure.

Referring now to FIG. 10, a cross-sectional view of the third intermediate product 60 created in the fourth sub-step 208 is shown. In one embodiment, the outer jacket 58 extends around the circumference of the second intermediate product 56. In one embodiment, the outer jacket 58 is thicker than the jacket sub-layer 54 and/or the braided layer 50.

Figure 11:
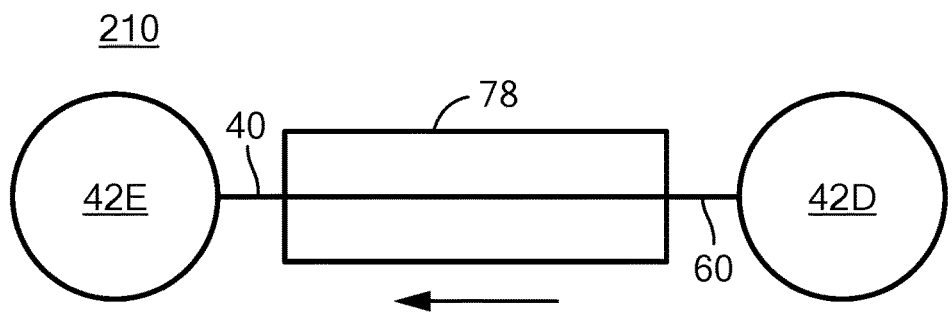
FIG. 11 is a stylized view of the fifth sub-step of the first step of the exemplary method of FIG. 2 in accordance with the present disclosure.
Figure 12:
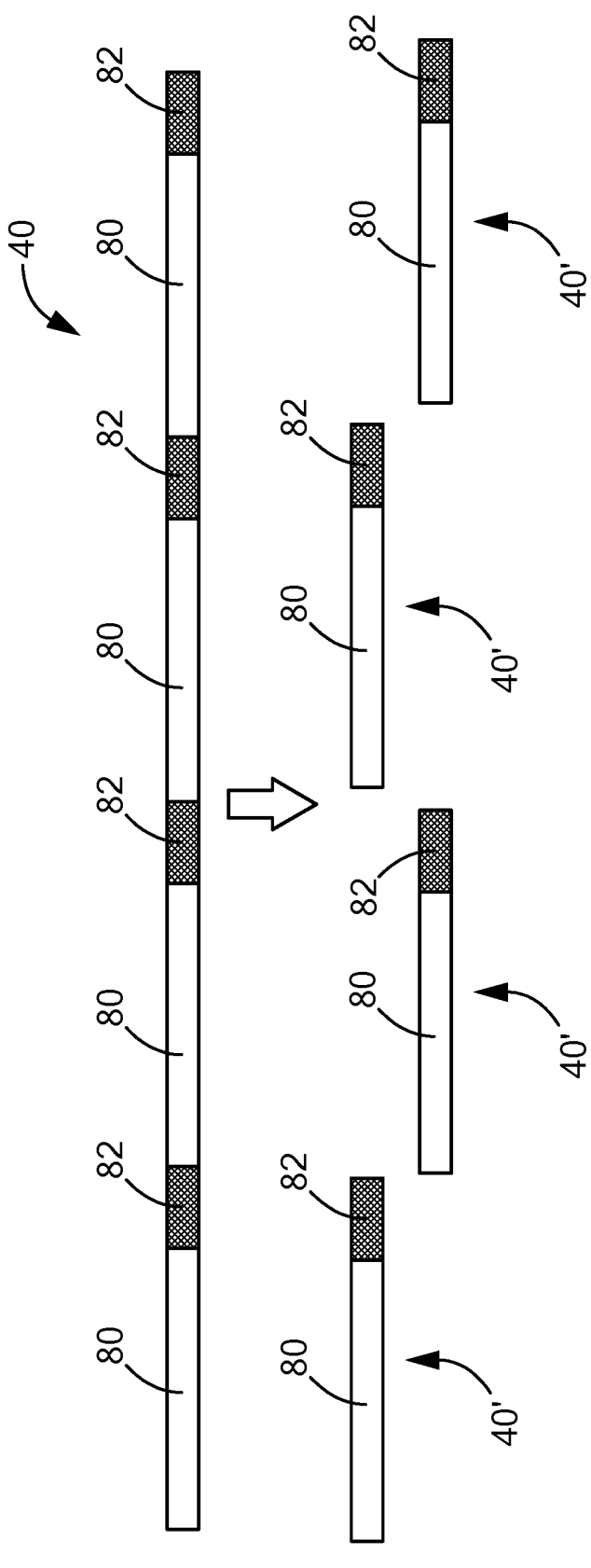
FIG. 12 is a stylized view of a second step of the exemplary method of FIG. 2 in accordance with the present disclosure.

Referring now to FIG. 11, the fifth sub-step 210 of the method of FIG. 2 is shown in greater detail. In this sub-step 210, at least a portion of the third intermediate product 60 is subjected to thermal treatment to crystallize the PET of the jacket sub-layer 54 as the third intermediate product 60 passes from the fourth reel 42D to a fifth reel 42E. In one embodiment, the third intermediate product 60 is heated by a heating element 78. In one embodiment, the heating element 78 is a heating chamber within which is a heat source such as one or more lasers, induction heaters, heat exchangers, or the like. In another embodiment, the heating element 78 is an in-line chamber. As discussed above, heating the jacket sub-layer 54 to a temperature above the $T_g$ of the material (for example, PET) induces a transition from the amorphous or semi-crystalline state to the crystalline state. Thus, heating the jacket sub-layer 54 causes the catheter tubing 40 in the heated segment(s) to become stiffer than the non-heated segment(s) and/or segment(s) heated to a lesser extent. Discrete portions of the third intermediate product 60 may be heated, or the third intermediate product may be passed through the heating element 78. The degree of stiffness or flexibility (that is, the degree of crystallization) of the third intermediate product 60, the number and location of segment(s) with increased stiffness, and/or other physical properties may be determined by the reel-to-reel speed, temperature to which the segment(s) are heated, location(s) of discrete heating, temperature used, time for which the segment(s) are heated, etc. Further, the reel-to-reel speed may be adjusted to produce real-time changes in the physical properties of desired segment(s) of the third intermediate product 60. Crystallization changes of various degrees may be made in predetermined patterns. For example, a segment of low flexibility/high crystallization may be created every three feet of the third intermediate product 60, a segment of medium flexibility/medium crystallization may be created between segments of low flexibility/high crystallization, a transitional segment may be created with increasing stiffness/crystallization, or the like). Thus, repeatable patterns of relative flexibilities (that is, repeatable segments of high, low, and/or intermediate flexibilities along) may be created along the length of catheter tubing in intervals that allows the catheter tubing 40 to be cut into a plurality of sub-lengths 40' of catheter tubing (as shown in FIG. 12), with each sub-length of catheter tubing 40' having the same characteristics (for example, segments of different flexibilities). Further, after thermal treatment, the third intermediate product 60 (or at least those portion(s) subjected to thermal treatment) is actively or passively cooled. In one non-limiting example, the catheter tubing 40 may be passed from the fifth reel 42E through a cooling chamber, or the fifth reel 42E with the catheter tubing 40 may be placed inside a cooling chamber or otherwise cooled. Additionally or alternatively, the catheter tubing 40 (either on or separate from the fifth reel 42E) may simply be removed from exposure to the heating element(s) and allowed to cool at room temperature. Upon completion of the fifth sub-step 210, the total length of the catheter tubing 40 having segments with varying flexibilities has been assembled.

Figure 13:
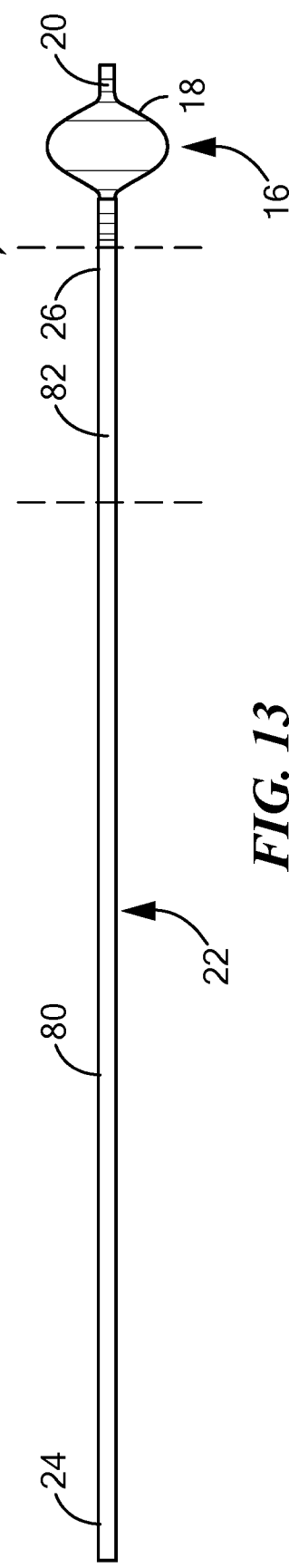
FIG. 13 is a side view of an exemplary medical device having a shaft assembled using a catheter tube created according to the method of FIG. 2 in accordance with the present disclosure.

Referring now to FIG. 13, a side view of an exemplary medical device 12 having an elongate body 22 assembled using a catheter tube 40 created according to the method of FIG. 2 is shown. The device 12 shown in FIG. 13 generally includes an elongate body 22 having a proximal portion 24 and a distal portion 26 and a treatment element 18 coupled to the distal portion 26. In one embodiment, the treatment element 18 includes a balloon 18 and at least one electrode 20. However, it will be understood that the treatment element 18 may be different than the non-limiting example shown in FIG. 13. The elongate body 22 is assembled using the catheter tubing 40 created according to the method of FIG. 2 (and described in FIGS. 3-11). Thus, the elongate body 22 includes at least one segment 80 having a first characteristic, such as a first flexibility, and at least one segment 82 having a second characteristic, such as a second flexibility. In the non-limiting example, shown in FIG. 2, the elongate body 22 has a first segment 80 in the proximal portion 24 (and which may also extend into the distal portion 26) in which the catheter tube 40 was heated to crystallize at least the jacket sub-layer 54, and a second segment 82 in the distal portion 26 in which the catheter tube 40 was not heated, or was heated to a lower temperature and/or for a longer period of time that the catheter tube 40 in the first segment 80. Therefore, the second segment 82 is more flexible than the first segment 78. In some embodiments, the elongate body 22 includes alternating flexible and stiff segments. In some embodiments, the elongate body 22 includes at least one transition segment having a gradient of flexibility values to provide a transition between adjacent segments. Further, as discussed above, in some embodiments a segment may both include an area in which at least the jacket sub-layer 54 is crystallized and an area in which the braided layer 50 is denser, thicker, such that the segment is very stiff and resists deformation more effectively than a flexible segment and/or even a segment in which the jacket sub-layer 54 only is crystallized. Further, it will be understood that other combinations of mechanical characteristics may be used.

Figure 14:
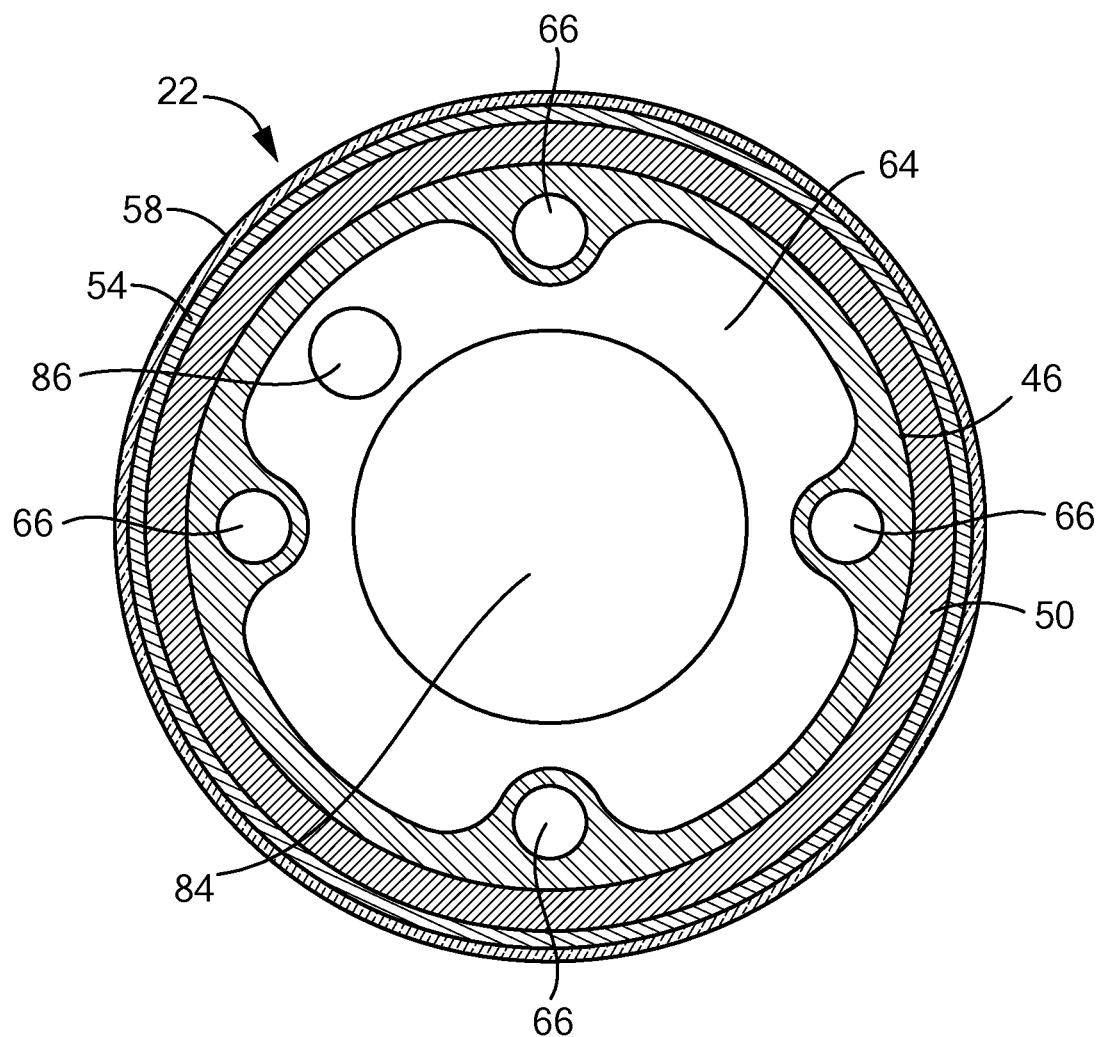
FIG. 14 is a cross-sectional view of the shaft of the medical device of FIG. 12.

Referring now to FIG. 14, a cross-sectional view of the elongate body 22 of the exemplary device 12 of FIG. 13 is shown. In one embodiment, the elongate body 22 includes a main lumen 64 and two minor lumens 66, which are each defined by a multi-lumen base layer 46. The elongate body further includes a braided layer 50, a jacket sub-layer 54, and an outer jacket 58. Further, in one embodiment, the elongate body 22 includes a fluid delivery lumen 84 and a fluid return lumen 86, such as may be used if the device 12 is used with a cryotreatment system.

Figure 15:
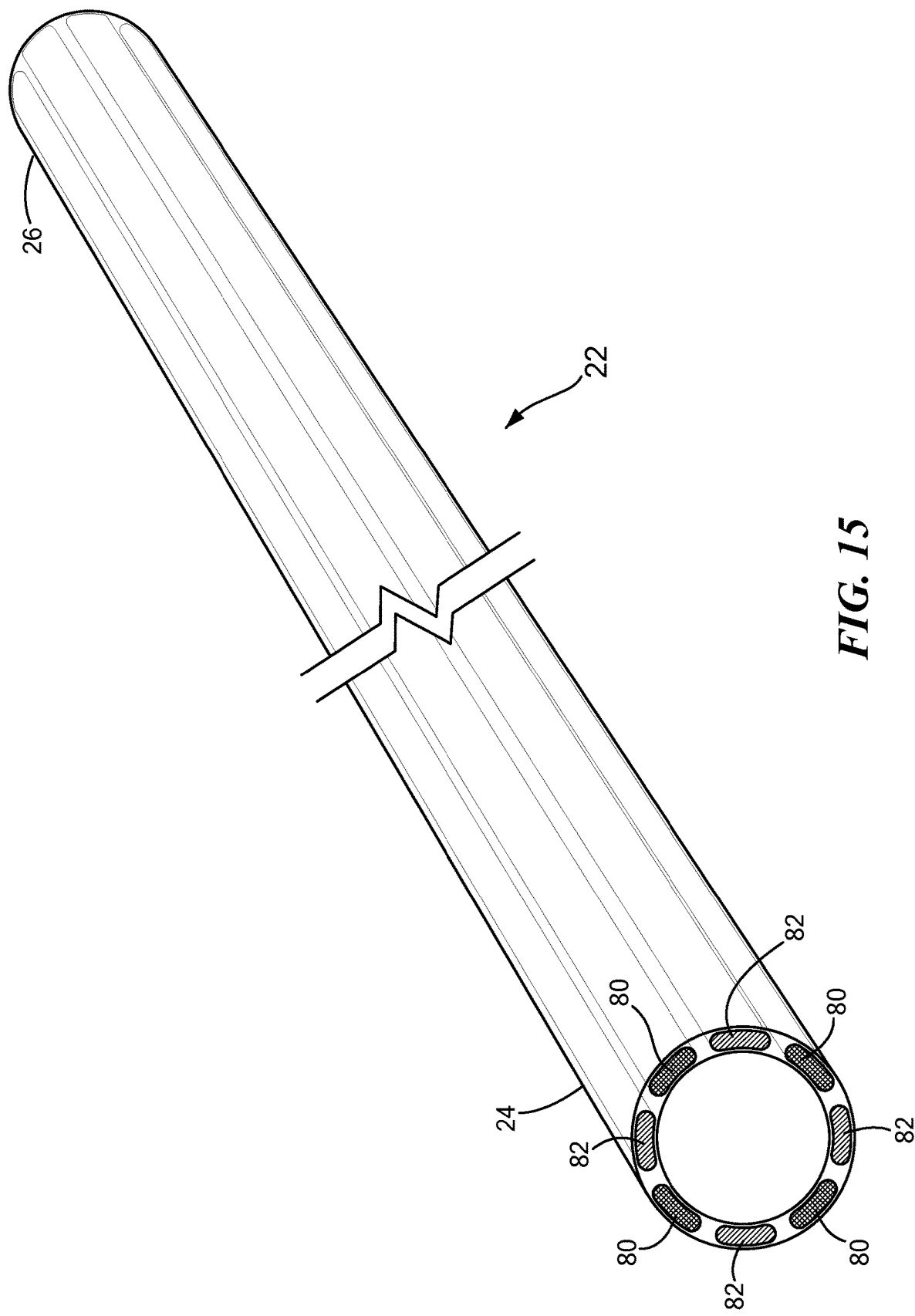
FIG. 15 is a cross-sectional and perspective view of another exemplary shaft of a medical device assembled using a catheter tube created according to the method of FIG. 2 in accordance with the present invention. in accordance with the present disclosure, the shaft having a plurality of longitudinal portions of different rigidities.

Referring now to FIG. 15, another exemplary embodiment of a shaft of a medical device assembled using a catheter tube created according to the method of FIG. 2 is shown. The shaft 22 is assembled in the same, or in substantially the same, manner as described above. However, in the embodiment shown in FIG. 15, the shaft 22 includes a plurality of longitudinal portions (or stripes) of different or alternating rigidities. In one embodiment, the shaft 22 includes a plurality of first longitudinal portions 80 having a first rigidity and a plurality of second longitudinal portions 82 having a second rigidity that is different than the first rigidity. In one non-limiting example, the shaft 22 includes four first longitudinal portions 80 and four second longitudinal portions 82, although it will be understood that any number of first and second longitudinal portions 80, 82 may be used. Further, the shaft 22 may also include one or more longitudinal portions having different rigidities than the first and second rigidities. Each longitudinal portion or stripe may extend from the distal portion 26 of the shaft 22 to the proximal portion 24 of the shaft 22. Put another way, each longitudinal portion may have the same length as, or be coextensive with, the shaft 22. Alternatively, each longitudinal portion may have a length that is less than the length of the shaft 22. Further, in one embodiment the longitudinal portions are symmetrically radially arranged about the longitudinal axis of the shaft 22. For example, in the embodiment shown in FIG. 15, the first longitudinal portions 80 are arranged at approximately 90° from each other and the second longitudinal portions 82 are also arranged at approximately 90° from each other and between the first longitudinal portions 80. In another embodiment, the longitudinal portions are non-symmetrically or randomly arranged about the longitudinal axis of the shaft 22.

In one embodiment, a method of manufacturing a length of catheter tubing comprises: extruding a base layer; overlaying a braided layer on the base layer; overlaying a sub-jacket layer over the braided layer; overlaying an outer jacket on the jacket sub-layer; and heating at least a portion the jacket sub-layer to change a characteristic of the length of catheter tubing.

In one aspect of the embodiment, the method is a reel-to-reel method.

In one aspect of the embodiment, the method further comprises cutting the length of catheter tubing to a plurality of sub-lengths of catheter tubing, each sub-length of catheter tubing being configured for use as an elongate body of a medical device. In one aspect of the embodiment, the medical device is a cardiac ablation catheter.

In one aspect of the embodiment, the base layer is at a first reel after the base layer is extruded.

In one aspect of the embodiment, overlaying the braided layer on the base layer includes passing the base layer from the first reel to a second reel, the base layer and the braided layer together being a first intermediate product; overlaying the jacket sub-layer on the braided layer includes passing the first intermediate product from the second reel to a third reel, the first intermediate product and the jacket sub-layer together defining a second intermediate product; overlaying the outer jacket on the jacket sub-layer including passing the second intermediate product from the third reel to a fourth reel, the second intermediate product and the jacket sub-layer together defining a third intermediate product; and heating the at least one portion of the jacket sub-layer includes passing the third intermediate product from the fourth reel to a fifth reel.

In one aspect of the embodiment, the third intermediate product is passed through a heating element.

In one aspect of the embodiment, the base layer includes a plurality of lumens.

In one aspect of the embodiment, the sub-jacket layer is at least partially composed of a crystallizable material.

In one aspect of the embodiment, the crystallizable material is polyethylene terephthalate (PET) and heating at least a portion the jacket sub-layer to change a characteristic of the length of catheter tubing includes crystallizing at least a portion of the PET.

In one aspect of the embodiment, heating at least a portion the jacket sub-layer includes heating the PET to a temperature above its glass transition temperature.

In one aspect of the embodiment, an entirety of the jacket sub-layer is heated.

In one aspect of the embodiment, less than an entirety of the jacket sub-layer is heated.

In one aspect of the embodiment, the jacket sub-layer is heated such that a plurality of segments having alternating flexibilities are created in a repeated pattern.

In one aspect of the embodiment, the jacket sub-layer is heated such that at least one segment having a first flexibility and at least one segment having a second flexibility are created, the first flexibility and the second flexibility being different.

In one embodiment, a method of manufacturing a length of catheter tubing comprises: extruding a base layer and passing the base layer to a first reel; overlaying a braided layer on the base layer as the base layer passes from the first reel to a second reel, the braided layer and base layer together being a first intermediate product; overlaying a sub-jacket layer over the braided layer of the first intermediate product as the first intermediate product passes from the second reel to a third reel, the sub-jacket layer and the first intermediate product together being a second intermediate product; overlaying an outer jacket on the jacket sub-layer of the second intermediate product as the second intermediate product passes from the third reel to a fourth reel, the outer jacket and the second intermediate product together being a third intermediate product; and heating at least a portion the jacket sub-layer of the third intermediate product as the third intermediate product passes from the fourth reel to a fifth reel to change a characteristic of the length of catheter tubing.

In one aspect of the embodiment, heating at least a portion of the jacket sub-layer includes passing the third intermediate product through a heating element between the fourth reel and the fifth reel.

In one aspect of the embodiment, the heating element is a reflow tower.

In one aspect of the embodiment, heating at least a portion of the jacket sub-layer includes adjusting a speed at which the third intermediate product passes from the fourth reel to the fifth reel and adjusting a time at which the at least a portion of the jacket sub-layer is exposed to the heating element.

In one embodiment, a method of manufacturing an elongate body of a medical device comprises: extruding a base layer, the base layer including a main lumen at a plurality of minor lumens, each of the main lumen and the plurality of minor lumens being without a liner; overlaying a braided layer on the base layer; overlaying a sub-jacket layer over the braided layer, the jacket sub-layer being at least partially composed of a crystallizable material; overlaying an outer jacket on the jacket sub-layer, the outer jacket being at least partially composed of a material that resists crystallization; heating the jacket sub-layer to change a flexibility of at least a portion of the length of catheter tubing; and cutting the length of catheter tubing into a plurality of sub-lengths of catheter tubing.

The details of one or more aspects of the disclosure are set forth in the accompanying drawings and the description below. Other features, objects, and advantages of the techniques described in this disclosure will be apparent from the description and drawings, and from the claims.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of manufacturing a length of catheter tubing, the method comprising:
   extruding a base layer, wherein the base layer includes a plurality of lumens;
   overlaying a braided layer on the base layer;
   overlaying a jacket sub-layer over the braided layer;
   overlaying an outer jacket on the jacket sub-layer; and
   heating at least a portion of at least one selected from the group consisting of the base layer, outer jacket layer, and jacket sub-layer to change a characteristic of the length of catheter tubing.

2. The method of claim 1, wherein the method is a reel-to-reel method.

3. The method of claim 1, further comprising cutting the length of catheter tubing to a plurality of sub-lengths of catheter tubing, each sub-length of catheter tubing being configured for use as an elongate body of a medical device.

4. The method of claim 3, wherein the medical device is a cardiac ablation catheter.

5. The method of claim 1, wherein the base layer is at a first reel after the base layer is extruded.

6. The method of claim 5, wherein:
   overlaying the braided layer on the base layer includes passing the base layer from the first reel to a second reel, the base layer and the braided layer together being a first intermediate product;
   overlaying the jacket sub-layer on the braided layer includes passing the first intermediate product from the second reel to a third reel, the first intermediate product and the jacket sublayer together defining a second intermediate product;
   overlaying the outer jacket on the jacket sub-layer including passing the second intermediate product from the third reel to a fourth reel, the second intermediate product and the jacket sub-layer together defining a third intermediate product; and
   heating the at least a portion of the jacket sub-layer includes passing the third intermediate product from the fourth reel to a fifth reel.

7. The method of claim 6, where the third intermediate product is passed through a heating element.

8. The method of claim 1, wherein the sub-jacket layer is at least partially composed of a crystallizable material.

9. A method of manufacturing a length of catheter tubing, the method comprising:
   extruding a base layer;
   overlaying a braided layer on the base layer;
   overlaying a jacket sub-layer over the braided layer, wherein the jacket sub-layer is at least partially composed of a crystallizable material;
   overlaying an outer jacket on the jacket sub-layer; and
   heating at least a portion of at least one selected from the group consisting of the base layer, outer jacket layer, and jacket sub-layer to change a characteristic of the length of catheter tubing,
   wherein the crystallizable material is polyethylene terephthalate (PET) and heating at least a portion the jacket sub-layer to change a characteristic of the length of catheter tubing includes crystallizing at least a portion of the PET.

10. The method of claim 9, wherein heating at least a portion the jacket sub-layer includes heating the PET to a temperature above its glass transition temperature.

11. The method of claim 10, wherein an entirety of the jacket sub-layer is heated.

12. The method of claim 10, wherein less than an entirety of the jacket sub-layer is heated.

13. The method of claim 10, wherein the jacket sub-layer is heated such that a plurality of segments having alternating flexibilities are created in a repeated pattern.

14. The method of claim 10, wherein the jacket sub-layer is heated such that at least one segment having a first flexibility and at least one segment having a second flexibility are created, the first flexibility and the second flexibility being different.

15. A method of manufacturing a length of catheter tubing, the method comprising:
   extruding a base layer and passing the base layer to a first reel;
   overlaying a braided layer on the base layer as the base layer passes from the first reel to a second reel, the braided layer and base layer together being a first intermediate product;
   overlaying a sub-jacket layer over the braided layer of the first intermediate product as the first intermediate product passes from the second reel to a third reel, the sub-jacket layer and the first intermediate product together being a second intermediate product;
   overlaying an outer jacket on the jacket sub-layer of the second intermediate product as the second intermediate product passes from the third reel to a fourth reel, the outer jacket and the second intermediate product together being a third intermediate product; and
   heating at least a portion the jacket sub-layer of the third intermediate product as the third intermediate product passes from the fourth reel to a fifth reel to change a characteristic of the length of catheter tubing,
   wherein heating at least a portion of the jacket sub-layer includes passing the third intermediate product through a heating element between the fourth reel and the fifth reel, and
   wherein heating at least a portion of the jacket sub-layer includes adjusting a speed at which the third intermediate product passes from the fourth reel to the fifth reel and adjusting a time at which the at least a portion of the jacket sub-layer is exposed to the heating element.

16. The method of claim 15, wherein the heating element is a reflow tower.

17. A method of manufacturing an elongate body of a medical device, the method comprising:
- extruding a base layer, the base layer including a main lumen land a plurality of minor lumens, each of the main lumen and the plurality of minor lumens being without a liner;
- overlaying a braided layer on the base layer;
- overlaying a sub-jacket layer over the braided layer, the jacket sub-layer being at least partially composed of a crystallizable material;
- overlaying an outer jacket on the jacket sub-layer, the outer jacket being at least partially composed of a material that resists crystallization;
- heating the jacket sub-layer to change a flexibility of at least a portion of the length of catheter tubing; and
- cutting the length of catheter tubing into a plurality of sub-lengths of catheter tubing.

\* \* \* \* \*